United States Patent [19]

Glonek et al.

[11] Patent Number: 4,914,088
[45] Date of Patent: Apr. 3, 1990

[54] DRY EYE TREATMENT SOLUTION AND METHOD

[76] Inventors: Thomas Glonek, 803 Highland Ave., Oak Park, Ill. 60304; Jack V. Greiner, 208 Stearns Hill Rd., Waltham, Mass. 02154; Donald R. Korb, 10 Brimmer St., Boston, Mass. 02108

[21] Appl. No.: 111,874

[22] Filed: Oct. 23, 1987

Related U.S. Application Data

[63] Continuation-in-part of Ser. No. 33,185, Apr. 2, 1987, abandoned.

[51] Int. Cl.$^4$ .............................................. A61K 31/66
[52] U.S. Cl. .......................................... 514/76; 514/75
[58] Field of Search .................................... 514/75, 76

[56] References Cited

U.S. PATENT DOCUMENTS 4,421,748 12/1983 Trager .............................. 424/78 X
4,677,099 6/1987 Shinitzky ........................... 514/76 X Primary Examiner—William R. Dixon, Jr.
Assistant Examiner—James M. Hunter, Jr.
Attorney, Agent, or Firm—Robert L. Goldberg

[57] ABSTRACT

A method and composition for treating dry eye. The method comprises addition of a positively or negatively charged, complex phospholipid to the ocular surface of the eye. The phospholipid is desirably added in a treatment composition, preferably in the form of an aqueous emulsion. It is believed that the phospholipid component of the treatment composition permits replication of a tear film.

27 Claims, No Drawings

DRY EYE TREATMENT SOLUTION AND METHOD

CROSS REFERENCE TO RELATED APPLICATION

This application is a continuation-in-part of copending U.S. patent application Ser. No. 07/033,185 filed Apr. 2, 1987 now abandoned.

BACKGROUND OF THE INVENTION

1. Introduction

This invention relates to treatment of a condition known as dry eye and more particularly, to the treatment of dry eye by topical application of certain charged phospholipids to the ocular surface.

2. Description of the Prior Art

It is known that dry eye is a condition of the eye and or the adnexa that usually causes a feeling of discomfort such as ocular dryness, grittiness, burning, soreness or scratching, dependent upon the subject and his condition. Many theories have been offered to explain the possible causes of dry eye. These theories range from the simple to the complex and include inadequate Meibomian gland secretion, insufficient tear volume, mucous deficiency, evaporative losses from the tear film and failure to form an adequate tear film. Proposed causes for dry eye, treatment and symptoms are all described in a compendium of papers on the subject edited by Holly, *The Preocular Tear Film In Health, Disease, and Contact Lens Wear*, The Dry Eye Institute, Lubock, Texas, 1986, incorporated herein by reference.

The most common treatment for dry eye involves alleviation of dry eye sumptoms by topical application of a tear substitute that adds a volume of liquid to the anterior surface of the eye and related adnexa. Typical tear substitute compositions comprise water soluble, aqueous polymer compositions. Such compositions include, for example, saline solutions of polyvinyl alcohols, hydroxypropylmethyl celluloses or carboxymethyl celluloses. U.S. Pat. No. 4,421,748 teaches an artificial tear composition comprising an aqueous hypotonic solution of lecithin and a viscosity adjusting agent such as a solution soluble cellulose.

Methods used to quantify the effectiveness of tear substitutes for dry eye treatment solutions have not been standardized, and many methods used in the art to quantify the results obtained with such tear-substitute compositions are often inaccurate. For this reason, it is known that reported relief of dry eye symptoms using known tear substitutes varies considerably from subject to subject, and regardless of the method used to quantify relief using a tear substitute, relief often does not exceed several minutes.

The symptoms associated with dry eye are often exacerbated with subjects using contact lenses. In some cases, contact lens intolerance is caused in part or in total by the condition of dry eye and the symptoms thereof. For many subjects, contact lens intolerance is not overcome by topical application of tear substitutes.

For the reasons given above, there is a need for improved compositions and processes for dry eye treatment. In particular, there is a need for a dry-eye-treatment composition that is easy to use, that provides a longer period of relief from dry eye symptoms, and which permits use of contact lenses by subjects having an intolerance to contact lens use due to a dry eye condition or symptoms.

SUMMARY OF THE INVENTION

The subject invention provides an improved dry eye treatment process and composition. The invention is based in part upon a means for correcting a principal deficiency in the tear film by topical application to the ocular surface of a complex phospholipid having a net positive or negative charge under conditions of use, which phospholipid, in contact with the ocular surface, is capable of replicating a tear film layer that is believed to be functionally equivalent to the tear film layer present in a healthy eye.

The tear film over the eye is reported to be a complex coating comprising three separate layers. The inner layer in contact with the ocular surface of the eye is reported to be primarily composed of mucous and is believed to render the hydrophobic epithelial cell surface hydrophilic. It is possible that this layer also contains other materials including phospholipid derivatives. The middle layer of the tear film is an aqueous layer. This layer is the thickest portion of the tear film and is a source of moisture for the eye and is further believed to function as an optical planarizing layer. The outer layer of the tear film, at its interface with the atmosphere and the eye, is an oily, naturally occurring lipid layer. The lipid layer is reported to act as a barrier that prevents evaporation of the aqueous layer, (Mishima and Maurice: The Oily Layer of The Tear Film and Evaporation From the Corneal Surface, Exp. Eye Res. 1961; 1: 39–45).

The lipid component of the tear film is believed primarily to originate from secretions of the Meibomian glands. It is formed from these secretions and is continuously replenished over the aqueous layer of the tear film during blinking due to the eyelid spreading the lipid over the surface of the eye. By constantly spreading the lipid over the eye during blinking, the tear film is maintained, and evaporation of the aqueous middle layer of the tear film is minimized.

A cause of dry eye is believed to result from a deficiency in the lipid layer. This deficiency may result from an inadequacy in the quantity of secretion from the Meibomian glands or an inadequacy in the quality of the secretion. Regardless of the cause of the deficiency, it is believed that the compromised layer fails to act as an adequate barrier against evaporation of the aqueous portion of the tear film thus resulting in one form of the condition known as dry eye.

With recognition of the most prevalent causes of dry eye, the subject invention provides a dry eye treatment process and composition for practice of the process. The treatment process comprises topical application to the ocular surface of a complex phospholipid having a net positive or negative charge under conditions of use. The phospholipid is applied to the eye in any suitable manner, and is typically applied in the form of a treatment composition such as a solution, if sufficiently soluble in its carrier liquid, a salve, ointment, suspension, or any other suitable form known to the art.

The preferred treatment composition is an emulsion. Upon contact of the phospolipid with the eye, it is believed that the phospholipid disperses over the ocular surface and forms a film over the eye that replicates the lipid layer that would be formed by the spreading of a naturally occurring lipid secreted from the Meibomian glands over the surface of the eye during blinking. Because the phospholipid, when applied to the eye, carries a net charge, it is believed that the aligned molecules repel each other such that complex aggregate formation is prevented and the integrity of the phospholipid film is maintained. It is believed that the film formed from the phospholipid acts as a barrier, reducing evaporation of the aqueous layer, thereby preserving the tear film.

Relief of dry eye symptoms by treatment in accordance with the invention is at least several fold the relief provided by prior art treatment compositions available in the marketplace. Films formed by application of the phospolipid to the eye are long lasting. Though it would be expected that a stable film formed over the eye would cause blurring, in practice, it has been found that blurring is no more severe than that blurring resulting from the application of prior-art-treatment compositions for dry eye symptoms or even physiological saline.

DESCRIPTION OF THE PREFERRED EMBODIMENTS

As described above, dry eye treatment in accordance with the invention is accomplished by topical application to the ocular surface of a complex phospholipid having a net charge under conditions of use. Topical application is by application of a treatment composition where the phospholipid is contained in a liquid vehicle. The composition may be in the form of an emulsion, solution, salve, ointment, etc. Preferably the phospholipid is homogeneously distributed throughout the vehicle and most preferably is in the form of an aqueous emulsion. The term "homogeneous" for purposes herein means that a separate layer of the phospholipid in the composition is not visible to the naked eye, though microscopic examination of preferred compositions of the invention might reveal a laminar structure, where layers are uniformly distributed throughout the composition.

Phospholipids, including their plasmalogen analogs, suitable for purposes of the invention are those known in the art to be complex and known to carry a net positive or negative charge under conditions of use.

It is known that complex phospolipids contain a polar group at one end of their molecular structure and a non-polar group at the opposite end of their molecular structure. A discussion of phospolipids can be found in Lehninger, *Biochemistry*, 2 ed., Worth Publishers, New York, pp. 279-306, incorporated herein by reference.

Many complex phospolipids are known to the art. They differ in size, shape and the electric charge of their polar head groups. Phosphoglycerides are compounds where one primary hydroxyl group of glycerol is esterified to phosphoric acid, and the other two hydroxyl groups are esterified with fatty acids. The parent compound of the series is, therefore, the phosphoric acid ester of glycerol. This compound has an asymmetric carbon atom and, therefore, the term phosphoglycerides includes stereoisomers.

All phosphoglycerides have a negative charge at the phosphate group at pH 7, and the $pK_a$ of this group is in the range of 1 to 2. The head groups of phosphatidylinositol, phosphatidylglycerol including diphosphatidylglycerols (having the common name cardiolipins) and the phosphatidylsugars have no electric charge, and all are polar because of their high hydroxyl group content. Because of the negative charge of the phosphate group and the absence of a charge in the head group, the net charge of each of these materials is negative, and these materials are within the scope of the invention. Likewise, the head group of phosphatidylserine contains an alpha-amino group ($pK_a=10$) and, a carboxyl group ($pK_a=3$) and therefore, the molecule contains two negative charges and one positive charge at pH 7.0, giving it a net negative charge whereby this compound is also within the scope of the invention.

Complex phospholipids having a net positive charge are also within the scope of this invention but are lesser preferred because of the price and scarcity of these compounds. Examples of positively charged complex phospholipids within the scope of the invention are those containing the basic acyl amino acid groups. Such compounds are a sub-group within the family of the O-aminoacylphosphatidylglycerols.

In contrast to the charged phospholipids, the head groups of phosphatidylethanolamine and phosphatidylcholine (lecithin) have a positive charge at pH 7, and, thus, at this pH, these two phosphoglycerides are dipolar zwitterions with no net electric charge. Such compounds are not within the scope of this invention.

Of the phospholipids discussed above, the net-charged phosphoglycerides are preferred for purposes of the invention. A more preferred class of phosphoglycerides are represented by the following generic formula:

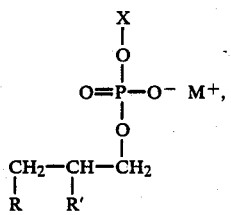

where R and R' are each fatty acid residues preferably having from 8 to 24 carbon atoms; X is hydrogen, a polyol or a 3'-O-aminoacylphosphatidylglycerol; and M is one equivalent of a countercation. R and R' are typically common natural fatty acids having an even or odd number of carbon atoms; they may be the same or may differ from each other; and they may be saturated, monounsaturated or polyunsaturated. Examples of fatty acid residues include palmitate, stearate, oleate, linoleate, octanoate, dodecate, lignocerate, etc.

The most preferred composition for purposes of this invention will be a mixture of complex phospholipids where each phospholipid component has a net negative charge. The most preferred phospholipids are the phosphatidylglycerols, including cardiolipins, and phosphatidylinositols.

Most phospholipids are water insoluble. However, for application to the eye, it is desirable that the phospholipid be homogeneously distributed throughout an aqueous medium. For those few phospholipids having a solubility within a useful concentration range for use as a treatment composition, a simple aqueous solution of the phospholipid in saline is satisfactory. For those phospholipids that are essentially water insoluble, an aqueous composition in the form of an emulsion may be used. An emulsion provides a treatment composition where the phase containing the phospholipid component is homogeneously distributed throughout the aqueous vehicle. An emulsion is readily formed by agitating one or more complex phospholipids and physiologic saline while warming the composition to a temperature in excess of the melting point of the phospholipid components. Agitation is continued at the elevated temperature until a homogeneous dispersion is obtained. Agitation is preferably mechanical agitation. Emulsification by sonification, which leads to the formation of unstable vesicles or liposomes, is undesirable. An emulsifying agent is desirably added to the formulation to stabilize the emulsion for long term storage, extended shelf life, and thermal stability. Phosphatidylcholine is a suitable emulsifying agent, though other emulsifying agents can be used if desired.

The concentration of the phospholipid in the treatment composition may vary within wide limits. A treatment composition containing the complex phospholipid in an amount as low as 0.01 weight percent provides some benefit. When the treatment composition is in the form of an emulsion, compositions containing the phospholipid in elevated concentrations approaching collapse of the emulsion into separate aqueous and phospholipid phases is possible. A clinically practical concentration range for the phospholipid in its vehicle varies from about 0.05 to 7.0 percent phospholipid by weight, and more preferably varies from about 0.1 and 5.0 weight percent. It should be noted that the most desired concentration for the phospholipid in the aqueous composition will vary from subject to subject.

Other additives may be present in the phospholipid treatment composition including neutral lipids such as one or more triglycerides, cholesterol esters, the natural waxes and cholesterol; higher molecular weight isoprenoids; stabilizers; preservatives; pH adjustors to provide a composition preferably having a pH between about 7.0 and 7.4; salt in sufficient concentration to form an isotonic composition; medicants; etc, all as would be obvious to those skilled in the art.

If the treatment composition is in the form of an emulsion, other additives in the treatment composition are preferably added prior to the formation of the emulsion using simple mixing techniques. The concentration of the additive is dependent upon the specific additive used and may vary between 0.00001 and 25.0 percent of the total composition.

For some subjects, neutral lipids comprise a desired class of additives because it is believed that they augment a second component of the lipid film located on the non-polar side of the complex phospholipid monolayer.

The method of application of the phospholipids of the invention to the subject is by topical application of the treatment composition to the ocular surface. Conventional means for dispensing the treatment composition are suitable. For example, application of the treatment composition may be by spray dispenser, eyedrop, sponge, etc. The amount of the phospholipid component of the treatment composition is small. If the treatment composition is in the form of an aqueous solution or emulsion, a single drop from a conventional eye dropper is satisfactory. Preferred dosage comprises application of one drop several times daily. The preferred dosage is believed to be capable of providing relief for periods of time at least several fold compared to commercial formulations, dependent upon the subject, as will be illustrated in the examples that follow.

Though not wishing to be bound by theory, it is believed that upon contact of the phospholipid treatment composition with the eye, a molecularly aligned monolayer complex phospholipid film forms over the aqueous layer of the tear film where the molecular alignment is augmented by the charge on the phospholipid. It is also possible that a portion of the phospholipid may be found in other portions of the tear film, such as in the first layer of the tear film is contact with the epithelial cell surface.

The invention will be better understood by reference to the examples that follow. In the examples, the efficacy of the treatment solution was determined using three test procedures described as follows:

EVALUATION OF BREAK UP TIME (BUT)

The normal tear film maintains an uninterrupted surface for a finite but adequate period of time to both protect the eye and to permit clear vision without blinking. Blinking restores and maintains the tear film. Certain conditions, such as forcibly restraining blinking, can cause the tear film to become discontinuous. The measurement of the time (in seconds) required for the tear film to evidence areas of discontinuity when blinking is suspended, is known as break up time (BUT). In the prior art, BUT has been measured by adding fluorescein, a fluorescent dye, and observing the stained tear film with light passed through a cobalt blue filter. However, the use of the dye in BUT evaluation presents another variable and was avoided for the tests reported herein. Instead, optical imaging was employed using a method described by Norn M. S.: "Tear Film Break Up Time. A Review". in Holly F, The Preocular Tear Film, 1986, pp. 52-54. The test is performed with an ophthalmometer as proposed by Norn without the use of the fluorescein dye. For each subject, a baseline BUT value was established. Larger BUTs represent a more stable tear film. The effectiveness of tear substitutes was investigated by comparison of BUT for various test solutions and controls versus a baseline BUT value for each eye tested. To evaluate BUT for a given test solution, the test solution is added to the eye by depressing the lower eyelid and placing one standard drop of the test solution into the inferior fornix (the space between the lower eyelid and the eye). The eyelid is then released, the subject is asked to blink at five second intervals, and one minute is allowed for the tear film to stabilize. The BUT measurement is then made as described by Norn with the ophthalmometer.

To obtain baseline data, the BUT test is performed prior to the addition of a test solution and then following the use of a test solution. Where multiple test solutions were used on a single subject on a given day, a recovery (waiting) time is required between trials. The recovery procedure involves irrigation (flushing) of the front surface of the eyes with sterile saline. Following irrigation, a recovery time of 20 minutes is provided to allow for stabilization of the tear film. If BUT is not consistent with initial baseline findings, further recovery time is provided until BUT times have returned to normal. In the examples, all BUT results are given in seconds.

MEASUREMENT OF VISUAL BLUR TIME (VBT)

Any liquid added to the tear film would be expected to cause a blur until the tear film returns to a form providing optimal optical characteristics. The test described below is intended to quantify blur time as a consequence of addition of a test solution.

To qualify a subject prior to the addition of a test solution, the subject is directed to a standard vision testing chart to determine if the subject's habitual tear film results in a visual blur with a measurable VBT. A subject qualifies if the habitual tear film does not produce a measurable VBT i.e., in the absence of a test solution, VBT is expected to be 0.

The test solution is added to the eye by depressing the lower eyelid and placing one standard drop into the inferior fornix (the space between the lower lid and eye). The eyelid is released, the subject's attention is directed to a standard vision testing chart, and the subject is asked to blink at 5 second intervals until the blur resolves. The time required for the blur to resolve, in seconds, is recorded as the VBT. This time may vary from several seconds to minutes. Times of less than 30 seconds are desirable. In the examples that follow, all times are in seconds.

EVALUATION OF LIPID THICKNESS (LT)

Quantification of the thickness of the lipid layer utilized methods reported by Guillon, J. P., "Tear Film Structure and Contact Lenses," in Holly F., *The Preocular Tear Film in Health, Disease and Contact Lens Wear*, Chapt. 85, pp. 914–939. This method allows approximation of the thickness of the lipid layer by observation of colored interference patterns over a representative portion of the corneal surface as set forth in the chart that follows:

| Color | Lipid Tickness (nm) |
|---|---|
| None | < 90 |
| Yellow | 90 |
| Yellow to Brown | 90–<170 |
| Blue | 170 |
| Intense Blue | >170 |

It should be recognized that subjectivity is involved in the reporting of observations of color. By necessity, color observation is subjective. Moreover, with this test, there are variations in the color at different locations on the corneal surface. Further, a lipid layer reflecting a minimal or fleeting blue coloration was considered to have a thickness of 170 nm. A lipid layer reflecting a more intense blue coloration, or a blue coloration over a greater portion of the test surface of the eye, was interpreted as having a thickness greater than 170 nm.

An effort was made to select subjects exhibiting dry eye symptoms with ocular findings indicating a deficient lipid layer and dysfunctional Meibomian glands. Again, baseline data was obtained for each eye prior to the addition of a test solution. Prior to the addition of any test solution, lipid thickness of a tear film was observed over a period of time generally ranging from 2 to 5 minutes. Observations were also made after 5, 15 and 60 minutes to determine if findings were consistent. For all tests and for each subject, the number of trials performed varied from 3 to 6, and an average of the results obtained are reported in the examples. If consistent findings were demonstrated, the subject qualified for study.

LT evaluation was made following instillation of one drop of treatment solution followed by observation until the blur produced by the solution had resolved. Observation times were standardized at 1 minute, 5 minutes, 15 minutes, 60 minutes and when possible, 180 minutes. Subjects presenting tear film conditions without detectable difference between eyes were selected, and one eye was evaluated with a control solution and the other with the test solution. Tests were of double blind design. Minor changes to the procedure described above are given in the examples.

EXAMPLE 1

This example sets forth a generalized procedure for the make-up of phospholipid test solutions and identifies test solutions used in the examples that follow.

A test phospholipid in a desired concentration was added to one liter of a borate buffered (pH 7.2), sorbic acid stabilized physiological saline (0.9% NaCl in sterile deionized water) with stirring. While stirring, the mixture was heated to a temperature immediately above the melting point of the test phospholipid to assist in its distribution in the saline. The mixture was maintained at elevated temperature with stirring for a time sufficient for the formation of a thickened and stable emulsion. This time typically varied from 20 to 60 minutes. The emulsion was then cooled to 24° C.

Test solutions prepared in accordance with the above procedure, controls used, and codes assigned to test solutions follow:

| | |
|---|---|
| CPC | A mixed phospholipid emulsion containing 7.0% of a product sold by Fisher Chemical as "Lecithin" and having a composition determined by analysis as follows: |

| | |
|---|---|
| Lysophosphatidic acid | 0.59% |
| Phosphatidylglycerol | 1.00% |
| Lysophosphatidylethanolamine | 0.74% |
| Phosphatidic acid | 7.08% |
| Cardiolipin | 2.14% |
| Phosphatidylethanolamine | 14.49% |
| Sphinogomeylin | 1.00% |
| Phosphatidylinositol | 9.58% |
| Phosphatidylcholine | 14.64% |
| Neutral lipids | balance |

| | |
|---|---|
| 0.7 CPC | CPC diluted 10 fold |
| CPCO | CPC diluted with 50% of a neutral lipid oil |
| 0.7 CPCO | 0.7 CPC diluted with 50% of a neutral lipid oil |
| PG-7 | 0.7% emulsion of phosphatidylinositol |
| PG-8 | 0.7% emulsion of phosphatidylglycerol |
| PG-10 | 0.7% solution of pure phosphatidylcholine (lecithin) |
| PG-11 | 0.7% solution of pure phosphatidylcholine (lecithin) diluted by 50% with neutral lipid |
| PG-15 | 0.7% solution of pure cardiolipin |
| PGS | Same as CPC but a second batch |
| 10PGS | PGS diluted 10 fold |
| 10PGSO | 10 PGS diluted with 50% of a neutral lipid oil |
| HTC | Control solution comprising commercial artiicial tear product available from Cooper Vision Pharmaceuticals Inc. believed to be a solution of water soluble polymer identified as HypoTears ® Dry Eye Solution. |
| UNC | Control solution comprising commercial saline product available from Cooper Vision Pharmaceuticals Inc. and identified as Unisol ® saline solution. |
| TGC | Control solution analyzed as an aqueous mixture of phospholipids consisting essentially of a major portion of phosphatidylcholine and a minor portion of lysophosphatidylinositol and lyso-phosphatidylcholine, and a hydroxyethyl cellulose in a hypotonic vehicle sold under the trademark TearGard ® by Bio Products Inc. |
| SESC | Sorbic acid preserved saline solution sold under the trademark Sensitive Eyes ® by Bausch and Lomb Inc. |

PG-7, PG-8, PG-15 and mixtures of these materials in equal concentration constitute the most preferred embodiment of the invention.

EXAMPLE 2

A subject was selected and Break-Up-Time, (BUT), Visual Blur Time (VBT) and Lipid Thickness (LT) were determined prior to adding a test solution to obtain baseline data with the following results obtained:

| | Baseline Data | |
|---|---|---|
| | Left Eye | Right Eye |
| BUT (sec.) | 8 | 11 |
| VBT (sec.) | 0 | 0 |
| LT (nm) | | |
| 1 min. | <90 | <90 |
| 5 mins. | <90 | <90 |
| 15 mins. | <90 | <90 |
| 60 mins. | <90 | <90 |
| 180 mins. | <90 | <90 |

Based upon the baseline data, the two eyes were considered equal for BUT, VBT and LT tests. The tests were then repeated on contralateral eyes to evaluate the HTC and 0.7 CPC test solutions. The HTC solution was added to the right eye and the 0.7 CPC solution added to the left eye. The results obtained follow:

| | Test Data | |
|---|---|---|
| | Left Eye (0.7 CPC) | Right Eye (HTC) |
| BUT (sec.) | 33 | 14 |
| VBT (sec.) | 13 | 15 |
| LT (nm) | | |
| 1 min. | ≧170 | <90 |
| 5 mins. | ≧170 | <90 |
| 15 mins. | ≧170 | <90 |
| 60 mins. | ≧170 | <90 |
| 180 mins. | 90–170 | <90 |

EXAMPLE 3

The procedures of Example 2 were repeated using 11 additional subjects. Again, HTC was added to the right eye (R) and 0.7 CPC was added to the left eye (L). The results obtained are reported in the following table:

In the above tests, an improvement in BUT was observed using 0.7 CPC. The data indicates that the tear film is more stable after the addition of 0.7 CPC than prior to the use of the composition and more stable than that achieved with HTC. The VBT is essentially the same as for the HTC commercial control product establishing that blurring is not exacerbated with the use of 0.7 CPC use. The LT shows improvement both following instillation of 0.7 CPC and following from 1 to 3 hours after instillation. The HTC control does not produce such improvement.

EXAMPLE 4

This example measures blur caused by the compositions of the invention at two different concentration levels with and without addition of a neutral lipid (oil). The example compares 4 compositions prepared in accordance with the invention with a commercial formulation for dry eye treatment. Further subjects were used for test purposes with results set forth in the following table:

| | | Visual Blur Time (sec.) | | | | |
|---|---|---|---|---|---|---|
| Patient | Baseline | HTC | 0.7 CPC | CPC | 0.7 CPCO | CPCO |
| 4-1 | 0 | 16 | 7 | 115 | 15 | 72 |
| 4-2 | 0 | 11 | 18 | 75 | 29 | 125 |
| 4-3 | 0 | 26 | 20 | 105 | 19 | 210 |
| 4-4 | 0 | 16 | 8 | 260 | 8 | 215 |
| 4-5 | 0 | 12 | 12 | 133 | 9 | 60 |
| 4-6 | 0 | 12 | 16 | 103 | 25 | 95 |
| 4-7 | 0 | 7 | 11 | 145 | 13 | 125 |
| 4-8 | 0 | 9 | 10 | 145 | 6 | 125 |
| 4-9 | 0 | 21 | 14 | 125 | 16 | 185 |
| 4-10 | 0 | 10 | 13 | 195 | 9 | 165 |
| 4-11 | 0 | 16 | 18 | 140 | 23 | 165 |
| 4-12 | 0 | 22 | 23 | 150 | 26 | 60 |

EXAMPLE 5

Another subject was tested to obtain baseline values for BUT, VBT and LT. The procedures of Example 2 were used. Following qualification for both the right and left eyes, test solutions of Example 1 were used and BUT, VBT and LT were determined for this subject following the installation of the test solution. The results are set forth in the following table:

| | | BUT (sec.) | | VBT (sec.) | | LT (in nm) | | | | | |
|---|---|---|---|---|---|---|---|---|---|---|---|
| Subject | Eye | Baseline | Test | Baseline | Test | Baseline | 1 Min. | 5 Min. | 15 Min. | 60 Min. | 180 Min. |
| 3-1 | R | 12 | 11 | 0 | 12 | <90 | 90 | 90 | <90 | <90 | <90 |
| | L | 14 | 32 | 0 | 12 | <90 | >170 | 170 | >170 | >170 | 170 |
| 3-2 | R | 11 | 27 | 0 | 16 | <90 | 90 | <90 | <90 | <90 | <90 |
| | L | 9 | 41 | 0 | 12 | <90 | >170 | >170 | >170 | >170 | 170 |
| 3-3 | R | 6 | 13 | 0 | 11 | <90 | <90 | <90 | <90 | <90 | <90 |
| | L | 4 | 43 | 0 | 11 | <90 | >170 | >170 | 170 | 170 | 90 < 170 |
| 3-4 | R | 8 | 23 | 0 | 16 | <90 | <90 | <90 | <90 | <90 | <90 |
| | L | 6 | 39 | 0 | 11 | <90 | >170 | 170 | 170 | 170 | 90 |
| 3-5 | R | 9 | 11 | 0 | 13 | <90 | 90 | 90 | 90 | <90 | <90 |
| | L | 7 | 32 | 0 | 10 | <90 | >170 | 170 | 170 | 170 | 90 |
| 3-6 | R | 11 | 5 | 0 | 22 | <90 | 90 | <90 | <90 | <90 | <90 |
| | L | 12 | 27 | 0 | 18 | <90 | >170 | >170 | 90 | 90 | 90 |
| 3-7 | R | 10 | 8 | 0 | 15 | <90 | <90 | <90 | <90 | <90 | <90 |
| | L | 9 | 14 | 0 | 14 | <90 | >170 | >170 | 170 | 90 | 90 |
| 3-8 | R | 16 | 11 | 0 | 15 | <90 | 90 | 90 | 90 | <90 | <90 |
| | L | 14 | 39 | 0 | 14 | <90 | >170 | 170 | 170 | 90 | 90 |
| 3-9 | R | 15 | 11 | 0 | 11 | <90 | <90 | <90 | <90 | <90 | <90 |
| | L | 13 | 32 | 0 | 9 | <90 | 170 | 170 | 90 < 170 | 90 < 170 | 90 < 170 |
| 3-10 | R | 9 | 8 | 0 | 12 | <90 | 90 | 90 | <170 | <170 | <170 |
| | L | 8 | 31 | 0 | 11 | <90 | >170 | >170 | >170 | 170 | 90 < 170 |
| 3-11 | R | 14 | 12 | 0 | 9 | <90 | <90 | <90 | <90 | <90 | <90 |
| | L | 12 | 20 | 0 | 12 | <90 | >170 | 170 | 90 < 170 | 90 < 170 | 90 < 170 |

| Solution | BUT (sec.) Baseline | BUT (sec.) Test | VBT (sec.) Baseline | VBT (sec.) Test | LT (in nm) Baseline | 1 Min. | 5 Min. | 15 Min. | 60 Min. | 180 Min. |
|---|---|---|---|---|---|---|---|---|---|---|
| HTC | 9 | 17 | 0 | 18 | <90 | 90 | 90 | <90 | <90 | <90 |
| UNC | 9 | 12 | 0 | 12 | <90 | 90 | 90 | <90 | <90 | <90 |
| PG-7 | 9 | 38 | 0 | 12 | <90 | >170 | >170 | >170 | >170 | 170 |
| PG-8 | 9 | 34 | 0 | 14 | <90 | >170 | >170 | >170 | 170 | 90 < 170 |
| PG-10 | 9 | 16 | 0 | 11 | <90 | 90 < 170 | 90 | <90 | <90 | <90 |
| PG-11 | 9 | 19 | 0 | 12 | <90 | 90 < 170 | 90 | <90 | <90 | <90 |
| PG-15 | 9 | 29 | 0 | 13 | <90 | >170 | >170 | >170 | >170 | 90 < 170 |
| 10 PGS | 9 | 30 | 0 | 10 | <90 | 90 < 170 | >170 | 90 < 170 | 90 < 170 | 90 < 170 |

EXAMPLE 6

The procedure of Example 5 was repeated with six additional subjects. The results are given below:

| Test Solution | Subject | BUT (sec.) Baseline | BUT (sec.) Test | VBT (sec.) Baseline | VBT (sec.) Test | LT (in nm) Baseline | 1 Min. | 5 Min | 15 Min. | 60 Min. | 180 Min. |
|---|---|---|---|---|---|---|---|---|---|---|---|
| HTC | | | | | | | | | | | |
| | 1 | 5 | 6 | 0 | 47 | 90 | 90 | 90 | 90 | 90 | 90 |
| | 2 | 8 | 9 | 0 | 30 | 90 | 90 | 90 | 90 | 90 | 90 |
| | 3 | 13 | 11 | 0 | 20 | 90 | >170 | 90 | 90 | 90 | 90 |
| | 4 | 8 | 6 | 0 | 12 | 90 | 90 | 90 | 90 | 90 | 90 |
| | 5 | 16 | 20 | 0 | 5 | 90 | >170 | 90 | 90 | 90 | 90 |
| | 6 | 10 | 7 | 0 | 9 | <90 | 90 | 90 | <90 | <90 | <90 |
| | Avg. | 10 | 10 | 0 | 20 | | | | | | |
| UNC | | | | | | | | | | | |
| | 1 | 5 | 5 | 0 | 14 | 90 | 90 | 90 | 90 | 90 | 90 |
| | 2 | 8 | 7 | 0 | 20 | 90 | 90 | 90 | 90 | 90 | 90 |
| | 3 | 13 | 6 | 0 | 10 | 90 | <90 | 90 | 90 | 90 | 90 |
| | 4 | 8 | 9 | 0 | 10 | 90 | 90 | 90 | 90 | 90 | 90 |
| | 5 | 16 | 17 | 0 | 4 | 90 | >170 | 90 | 90 | 90 | 90 |
| | 6 | 10 | 10 | 0 | 7 | <90 | 90 | <90 | <90 | <90 | <90 |
| | Avg. | 10 | 9 | 0 | 11 | | | | | | |
| PG-7 | | | | | | | | | | | |
| | 1 | 5 | 20 | 0 | 11 | 90 | >170 | >170 | >170 | >170 | 90–170 |
| | 2 | 8 | 23 | 0 | 13 | 90 | >170 | >170 | >170 | >170 | 90 < 170 |
| | 3 | 13 | 31 | 0 | 14 | 90 | >170 | >170 | >170 | >170 | >170 |
| | 4 | 8 | 33 | 0 | 11 | 90 | >170 | >170 | >170 | 90 < 170 | 90 < 170 |
| | 5 | 16 | 39 | 0 | 5 | 90 | >170 | >170 | >170 | >170 | 90 < 170 |
| | 6 | 10 | 26 | 0 | 9 | 90 | >170 | >170 | >170 | 90 < 170 | 90 < 170 |
| | Avg. | 10 | 29 | 0 | 11 | | | | | | |
| PG-8 | | | | | | | | | | | |
| | 1 | 5 | 15 | 0 | 13 | 90 | >170 | >170 | >170 | >170 | 90 < 170 |
| | 2 | 8 | 21 | 0 | 29 | 90 | >170 | >170 | >170 | >170 | 90 < 170 |
| | 3 | 13 | 37 | 0 | 39 | 90 | >170 | >170 | >170 | >170 | 170 |
| | 4 | 8 | 21 | 0 | 10 | 90 | >170 | >170 | >170 | 90 < 170 | 90 < 170 |
| | 5 | 16 | 51 | 0 | 5 | 90 | >170 | >170 | >170 | >170 | 90 < 170 |
| | 6 | 10 | 29 | 0 | 3 | 90 | >170 | >170 | >170 | 90 < 170 | 90 < 170 |
| | Avg. | 10 | 29 | 0 | 17 | | | | | | |
| PG-10 | | | | | | | | | | | |
| | 1 | 5 | 7 | 0 | 16 | 90 | 90 < 170 | 90 < 170 | 90 | 90 | 90 |
| | 2 | 8 | 10 | 0 | 11 | 90 | 90 < 170 | 90 < 170 | 90 | 90 | 90 |
| | 3 | 13 | 12 | 0 | 15 | 90 | >170 | 90 < 170 | 90 | 90 | 90 |
| | 4 | 8 | 10 | 0 | 7 | 90 | >170 | 90 | 90 | 90 | 90 |
| | 5 | 16 | 15 | 0 | 4 | 90 | >170 | >170 | 90 | 90 | 90 |
| | 6 | 10 | 11 | 0 | 6 | <90 | 90 | 90 | <90 | <90 | <90 |
| | Avg. | 10 | 11 | 0 | 10 | | | | | | |
| PG-11 | | | | | | | | | | | |
| | 1 | 5 | 6 | 0 | 16 | 90 | 90 < 170 | 90 < 170 | 90 | 90 | 90 |
| | 2 | 8 | 9 | 0 | 17 | 90 | 90 < 170 | 90 < 170 | 90 | 90 | 90 |
| | 3 | 13 | 13 | 0 | 10 | 90 | >170 | 90 | 90 | 90 | 90 |
| | 4 | 8 | 9 | 0 | 18 | 90 | >170 | 90 | 90 | 90 | 90 |
| | 5 | 16 | 16 | 0 | 5 | <90 | 90 < 170 | 90 | 90 | 90 | 90 |
| | 6 | 10 | 13 | 0 | 11 | <90 | 90 | 90 | <90 | <90 | <90 |
| | Avg. | 10 | 11 | 0 | 13 | | | | | | |
| PG-15 | | | | | | | | | | | |
| | 1 | 5 | 23 | 0 | 12 | 90 | >170 | >170 | >170 | 90 < 170 | 90 < 170 |
| | 2 | 8 | 17 | 0 | 21 | 90 | >170 | >170 | >170 | 90 < 170 | 90 < 170 |
| | 3 | 13 | 27 | 0 | 23 | 90 | >170 | >170 | >170 | >170 | 90 < 170 |
| | 4 | 8 | 31 | 0 | 10 | | | Not Done | | | |
| | 5 | 16 | 46 | 0 | 6 | | | Not Done | | | |
| | 6 | 10 | 31 | 0 | 7 | <90 | >170 | >170 | >170 | 90–170 | 90 < 170 |
| | Avg. | 10 | 29 | 0 | 13 | | | | | | |
| 10 PGS | | | | | | | | | | | |
| | 1 | 5 | 16 | 0 | 12 | 90 | >170 | >170 | >170 | 90 < 170 | 90 < 170 |

-continued

| Test Solution | Subject | BUT (sec.) Baseline | BUT (sec.) Test | VBT (sec.) Baseline | VBT (sec.) Test | LT (in nm) Baseline | 1 Min. | 5 Min | 15 Min. | 60 Min. | 180 Min. |
|---|---|---|---|---|---|---|---|---|---|---|---|
| | 2 | 8 | 14 | 0 | 8 | 90 | >170 | >170 | >170 | 90 < 170 | 90 < 170 |
| | 3 | 13 | 23 | 0 | 13 | 90 | >170 | >170 | 90 < 170 | 90 < 170 | 90 |
| | 4 | 8 | 23 | 0 | 9 | 90 | >170 | >170 | 90 < 170 | 90 < 170 | 90 |
| | 5 | 16 | 31 | 0 | 4 | 90 | >170 | >170 | 90 < 170 | 90 < 170 | 90 |
| | 6 | 10 | 21 | 0 | 16 | <90 | >170 | >170 | >170 | 90 | 90 |
| | Avg. | 10 | 21 | 0 | 9 | | | | | | |

Of particular interest in the above examples are the results obtained using the test solution identified as PG-10. PG-10 is a solution of pure phosphatidylcholine, a neutral phospholipid known commercially as lecithin. The results using this phospholipid are inferior to the results obtained using a charged phospholipid in accordance with the invention.

EXAMPLE 7

VBT was found to be 0. LT was found to be less than 90 nm.

BUT, VBT and LT were evaluated for test solutions identified in Example 1 using the procedures of Example 2. The results follow:

| Solution | BUT (sec.) Baseline | BUT (sec.) Test | VBT (sec.) Baseline | VBT (sec.) Test | LT (in nm) Baseline | 1 Min. | 5 Min. | 15 Min. | 60 Min. | 180 Min. |
|---|---|---|---|---|---|---|---|---|---|---|
| HTC | 10 | 14 | 0 | 17 | <90 | 90 | 90 | <90 | <90 | <90 |
| UNC | 10 | 12 | 0 | 13 | <90 | 90 | 90 | <90 | <90 | <90 |
| PG-7 | 10 | 31 | 0 | 11 | <90 | >170 | >170 | >170 | >170 | 170 |
| PG-8 | 10 | 30 | 0 | 13 | <90 | >170 | >170 | >170 | 170 | 90 < 170 |
| TGC | 10 | 13 | 0 | 175 | <90 | 90 | 90 | <90 | <90 | <90 |

EXAMPLE 8

The procedure of Example 7 was expanded to an additional five subjects with results as follow:

| Test Solution | Subject | BUT (sec.) Baseline | BUT (sec.) Test | VBT (sec.) Baseline | VBT (sec.) Test | LT (in nm) Baseline | 1 Min. | 5 Min. | 15 Min. | 60 Min. | 180 Min. |
|---|---|---|---|---|---|---|---|---|---|---|---|
| HTC | | | | | | | | | | | |
| | 1 | 7 | 13 | 0 | 18 | <90 | 90 | 90 | <90 | <90 | <90 |
| | 2 | 9 | 11 | 0 | 22 | <90 | 90 | 90 | <90 | <90 | <90 |
| | 3 | 14 | 13 | 0 | 6 | 90 | 90 < 170 | 90 < 170 | 90 | 90 | 90 |
| | 4 | 11 | 10 | 0 | 9 | 90 | 90 < 170 | 90 < 170 | 90 | 90 | 90 |
| | 5 | 9 | 13 | 0 | 13 | <90 | 90 | 90 | 90 | <90 | <90 |
| | Avg. | 10 | 12 | 0 | 10 | | | | | | |
| UNC | | | | | | | | | | | |
| | 1 | 7 | 10 | 0 | 14 | <90 | 90 | 90 | <90 | <90 | <90 |
| | 2 | 9 | 12 | 0 | 10 | <90 | 90 | 90 | <90 | <90 | <90 |
| | 3 | 14 | 11 | 0 | 8 | 90 | 90 < 170 | 90 < 170 | 90 | 90 | 90 |
| | 4 | 11 | 13 | 0 | 15 | 90 | 90 < 170 | 90 < 170 | 90 | 90 | 90 |
| | 5 | 9 | 11 | 0 | 9 | <90 | 90 | 90 | <90 | <90 | <90 |
| | Avg. | 10 | 11 | 0 | 13 | | | | | | |
| PG-7 | | | | | | | | | | | |
| | 1 | 7 | 37 | 0 | 13 | <90 | >170 | >170 | >170 | >170 | 90 < 170 |
| | 2 | 9 | 27 | 0 | 10 | <90 | >170 | >170 | >170 | >170 | 90 < 170 |
| | 3 | 14 | 29 | 0 | 9 | 90 | >170 | >170 | >170 | 170 | 90 < 170 |
| | 4 | 11 | 32 | 0 | 10 | 90 | >170 | >170 | >170 | 170 | 90 < 170 |
| | 5 | 9 | 36 | 0 | 8 | <90 | >170 | >170 | >170 | 170 | 90 < 170 |
| | Avg. | 10 | 32 | 0 | 10 | | | | | | |
| PG-8 | | | | | | | | | | | |
| | 1 | 7 | 32 | 0 | 11 | <90 | >170 | >170 | >170 | 170 | 90 < 170 |
| | 2 | 9 | 23 | 0 | 8 | <90 | >170 | >170 | >170 | >170 | 170 |
| | 3 | 14 | 31 | 0 | 7 | 90 | >170 | >170 | >170 | 170 | 170 |
| | 4 | 11 | 26 | 0 | 12 | 90 | >170 | >170 | >170 | 170 | 90 < 170 |
| | 5 | 9 | 28 | 0 | 9 | <90 | >170 | >170 | >170 | 170 | 90 < 170 |
| | Avg | 10 | 28 | 0 | 10 | | | | | | |
| TGC[2] | | | | | | | | | | | |
| | 1 | 7 | 12 | 0 | 240 | <90 | 90 | 90 | <90 | <90 | <90 |
| | 2 | 9 | 9 | 0 | 180 | <90 | 90 | 90 | <90 | <90 | <90 |
| | 3 | 14 | 11 | 0 | 60 | 90 | 90 < 170 | 90 < 170 | 90 | 90 | 90 |
| | 4 | 11 | 10 | 0 | 180 | 90 | 90 < 170 | 90 < 170 | 90 | 90 | 90 |
| | 5 | 9 | 12 | 0 | 240 | <90 | 90 | 90 | <90 | <90 | <90 |
| | Avg. | 10 | 11 | 0 | 180 | | | | | | |

An additional subject was selected and baseline BUT data collected. The right eye BUT was 9 seconds and the left, 10 seconds. Both eyes were considered equal.

EXAMPLE 9

Twenty subjects were selected that were both users and non users of contact lenses. Each was provided with treatment solution in 5 cc bottles blind coded for objectivity. The codes of Example 1 were used. The materials tested were as follows:

Coded Material
PGS
10 PGS
10 PGSO
CON
HTC

In these examples, sorbic acid preserved saline solution carrier was selected for preparation of the emulsions identified as 10 PGS, PGS and 10 PGSO in distinction to the compositions described in Example 1.

The solutions were evaluated for comfort and improvement of classic dry eye symptoms. Preference for lack of blur and other undesirable phenomena were noted. The following contralateral test plan was implemented:

| Day | Right Eye | Left Eye |
|---|---|---|
| 1-4 | CON | 10 PGSO |
| 5-8 | 10 PGSO | CON |
| 9-12 | 10 PGS | PGS |
| 13-16 | PGS | 10 PGS |

The results follow:

| Composition | Preference No. of Subjects |
|---|---|
| CON | 0 |
| 10 PGS | 13 |
| PGS | 1 |
| 10 PGSO | 4 |
| No choice | 2 |
| Total | 20 |

The majority of the subjects preferred the 10-PGS, but 4 (20% of population) preferred 10-PGSO (with the addition of oil).

EXAMPLE 10

The procedure of Example 9 was repeated with 6 additional subjects with solutions coded as follows:

Coded Material
10 PGS
PG-7
PG-10
SESC
TGC

The following contralateral test plan was used:

| Day | Right Eye | Left Eye |
|---|---|---|
| 1-4 | HTC | SESC |
| 5-8 | SESC | HTC |
| 9-12 | TGC | 10 PGS |
| 13-16 | 10 PGS | TGC |
| 17-20 | PG-7 | PG-10 |
| 21-24 | PG-10 | PG-7 |

The results follow:

| Composition | Preference No. of Subjects |
|---|---|
| HTC | 0 |
| SESC | 0 |
| TGC | 0 |
| 10PGS | 1 |
| PG-7 | 5 |
| PG-10 | 0 |
| No choice | 0 |
| Total | 6 |

EXAMPLE 11

The procedure of Example 9 was repeated with six additional subjects with solutions coded as follows:

Coded Material
HTC
TGC
SESC
10 PGS

The following contralateral test plan was implemented.

| Day | Right Eye | Left Eye |
|---|---|---|
| 1-4 | HTC | SESC |
| 5-8 | SESC | HTC |
| 9-12 | TGC | 10 PGS |
| 13-16 | 10 PGS | TGC |

The results were as follows:

| Composition | Preference No. of Subjects |
|---|---|
| HTC | 0 |
| SESC | 0 |
| TGC | 0 |
| 10 PGS | 6 |
| No choice | 0 |
| Total | 6 |

There are many forms of eye disease which are the result or which are associated with dry eye conditions. The phospholipid treatment compositions of the invention provide relief for these conditions. Evaluation of these compositions with subjects evidencing forms of superior limbal conjunctivitis, traumatized bulbar and palpebral conjunctiva, and related lid disease have shown significant relief from associated pain and also improvement in the tissue associated with these diseases. This is considered significant for the medical treatment of anterior segment surface disease.

We claim:

1. An artificial tear film over the surface of an eye comprising a first layer in direct contact with the ocular surface, an aqueous layer over the first layer, and a layer of a complex phospholipid having a net positive or negative charge over the aqueous layer.

2. The tear film of claim 1 where the phospholipid layer has polar groups extending towards the aqueous layer and non-polar groups extending away from the aqueous layer.

3. The tear film of claim 1 where the phospholipid layer is selected from the group of phosphatidylglycerols, phosphatidylinositols, diphosphatidylglycerols, phosphatidylsugars and mixtures thereof.

4. The tear film of claim 1 where the phospholipid layer is of a phospholipid conforming to the following general formula:

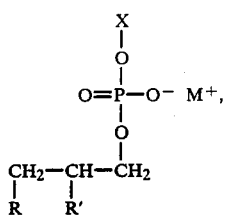

where R and R' are each fatty acid residues, X is hydrogen, a polyol or an 3'-O-aminoacylphosphatidylglycerol, and M is a cation.

5. The tear film of claim 4 where R and R' are the same.

6. The tear film of claim 1 where the phospholipid is phosphatidylglycerol.

7. The tear film of claim 1 where the phospholipid is phosphatidylinositol.

8. The tear film of claim 1 where the phospholipid is a cardiolipin.

9. A stable aqueous emulsion eye treatment composition having a pH of from about 7.0 to 7.4 containing one or more complex phospholipids having a net positive or negative charge under conditions of use in an amount of at least 0.01 percent by weight of the total weight of the treatment composition.

10. The treatment composition of claim 9 where the phospholipid composition contains the phospholipid in an amount of from 0.05 to 7.0 percent by weight.

11. The treatment composition of claim 9 containing a neutral lipid in addition to the phospholipid.

12. The treatment composition of claim 9 where the phospholipid is selected from the group of phosphatidylglycerols, phosphatidylinositols, diphosphatidylglycerols, phosphatidylsugars and mixtures thereof.

13. The treatment composition of claim 9 where the phospholipid conforms to the following general formula:

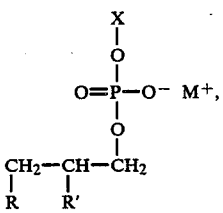

where R and R' are each fatty acid residues, X is hydrogen, a polyol or a 3'-O-aminoacylphosphatidylglycerol, and M is a cation.

14. The treatment composition of claim 13 where R and R' are the same.

15. The treatment composition of claim 9 where the phospholipid is phosphatidylglycerol.

16. The treatment composition of claim 9 where the phospholipid is phosphatidylinositol.

17. The treatment composition of claim 9 where the phospholipid is a cardiolipin.

18. A method for treating the eye comprising the formation of an artificial tear film over the eye by the topical application to the ocular surface of a treatment composition that contains one or more complex phospholipids having a net negative or positive charge under conditions of use in an amount of at least 0.01 percent by weight of the total weight of the treatment composition.

19. The dry eye treatment method of claim 18 where the aqueous composition is in the form of a stable aqueous emulsion.

20. The dry eye treatment method of claim 19 where the phospholipid composition contains the phospholipid in an amount of from 0.5 to 7.0 percent by weight.

21. The dye eye treatment method of claim 19 where the phospholipid is selected from the group of phosphatidylglycerol, phosphatidylinositol and cardiolipins.

22. The dry eye treatment method of claim 19 where the phospholipid conforms to the following general formula:

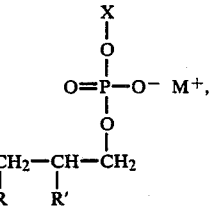

where R and R' are each fatty acid residues, X is hydrogen, a polyol or a 3'-O-aminoacylphosphatidylglycerol, and M is a cation.

23. The dry eye treatment method of claim 22 where R and R' are the same.

24. The dry eye treatment method of claim 22 where R and R' differ from each other.

25. The dry eye traatment method of claim 19 where the phospholipid is phosphatidylglycerol.

26. The dry eye treatment method of claim 19 where the phospholipid is phosphatidylinositol.

27. The dry eye treatment method of claim 19 where the phospholipid is a cardiolipin.

* * * * *